United States Patent [19]

Galat

[11] Patent Number: 5,157,030
[45] Date of Patent: Oct. 20, 1992

[54] RAPIDLY SOLUBLE ASPIRIN COMPOSITIONS AND METHOD

[76] Inventor: Alexander Galat, 1950 S. Ocean Dr., Hallandale, Fla. 33009

[21] Appl. No.: 398,413

[22] Filed: Aug. 25, 1989

[51] Int. Cl.⁵ .............................................. A61K 31/60
[52] U.S. Cl. ..................................... 514/165; 514/159; 424/43; 424/44; 424/466
[58] Field of Search ................... 514/159, 165; 424/44, 424/43, 466, 47

[56] References Cited

U.S. PATENT DOCUMENTS 4,687,662  8/1987  Schobel ............................... 514/159
4,942,039  7/1990  Duvall et al. ........................ 424/466

Primary Examiner—Jose G. Dees
Assistant Examiner—Deborah D. Carr
Attorney, Agent, or Firm—Bryan, Levitin, Franzino & Rosenberg

[57] ABSTRACT

The reaction rate between aspirin and an equimolar amount of alkaline compound in an aqueous medium is increased by the inclusion of a surface-active agent such as lecithin or an oxyethylene-oxypropylene polymer. As a result the aspirin is completely dissolved within the aqueous medium to increase its availability in the body and reduce damage to gastro-intestinal mucosa, the primary adverse side effect of aspirin.

13 Claims, No Drawings

RAPIDLY SOLUBLE ASPIRIN COMPOSITIONS AND METHOD

FIELD AND BACKGROUND OF THE INVENTION

The present invention relates in general to aspirin, and in particular to a new and useful composition and method for rapidly soluble aspirin.

The important role played by aspirin in the treatment and management of the two most common major diseases afflicting the world's population, i.e. arthritis and heart attacks, is well known. It is an effective analgesic and anti-inflammatory agent. In addition, its beneficial effect on the immune system makes aspirin a promising drug for the treatment of cancer, AIDS, cataracts, allergies and other diseases in which the immune system is involved. These valuable pharmacological properties makes aspirin the most widely used drug in the world.

Aspirin possesses side-effects, however, the true severity of which has been recognized only recently. Being a sparingly soluble substance (0.33 gm in 100 ml of water) particles of aspirin adhere to gastrointestinal mucosa causing lesions, gastric and duodenal ulcers and often massive bleeding and death. These side effects are persistent and cumulative and occur in nearly all patients using aspirin therapy. Gastroscopic and clinical studies confirm the topical nature of these side effects. (Lancet 2:1222, 1938; 1:539, 1959; August 1980; Brit. Med. J. 2:7, 1955; New England J. Medicine 258:219, 1958; The Amer. J. of Digestive Diseases, 1961; Pharmacology, 25, 1982; The Annals of Internal Medicine, Sept. 1988).

Corrosive effects of aspirin on gastrointestinal mucosa were recognized early in the history of aspirin therapy and attempts to produce soluble forms of this drug were made continuously since then. See U.S. Pat. No. 740,703 of 1903. These efforts were concentrated almost exclusively on the preparation of various soluble salts: lithium, sodium, potassium, calcium, magnesium and with organic amines and amino acids (lysine, ornithine). The main disadvantages of these salts was that, in contrast to aspirin itself, they were not stable. Most of them contain water of crystallization which produces an intramolecular hydrolysis resulting in the splitting of the molecule into salicylic and acetic acids. Attempts to prevent this decomposition by removing the water and forming anhydrous salts result in hygroscopic products which are difficult to handle, expensive to produce and require special expensive moisture-proof packaging of each individual dose. The cost of such products was very high and they could not compete with aspirin commercially. In addition, the use of these salts often involves the ingestion of undesirably high amounts of metallic elements.

More recently, attempts were made to obviate these disadvantages and side effects by simpler and less expensive means. Thus, aspirin tablets were coated with layers of buffering agents designed to neutralize the gastric acidity. Calcium carbonate, magnesium carbonate, magnesium hydroxide, sodium aluminum carbonate, sodium aluminum glycinate and the like, are thus in use in a number of commercial aspirin products. Clinical studies show that these methods are not effective, partly because it is not possible to coat a tablet with sufficient amounts of buffering agent to neutralize the gastric acid. Even if it were possible to do so, there is an immediate natural response which causes the production of more acid, often in larger amounts than originally present (acid rebound). But, more importantly, buffering agents do not prevent the insoluble particles of aspirin from adhering to the gastro-intestinal mucosa and causing corrosion. Another method used in commercial tablets is to entero-coat them to prevent the aspirin release in the stomach and to exert its effect in the intestine. This simply results in shifting the locus of side-effects from the stomach to the intestine.

As mentioned above, the manufacture of soluble salts of aspirin is complicated and costly. A typical example is the manufacture of the sodium salt of aspirin as disclosed in U.S. Pat. No. 3,985,792. The first step of this process consists in reacting aspirin with sodium bicarbonate in water, which forms a solution of the sodium salt. In the second step, this solution is treated with isopropanol and cooled to 5° C., which causes the crystallization of sodium acetylsalicylate dihydrate. The third step involves the filtration and the washing to the dihydrate. In the fourth step, the dihydrate, which is unstable, is dehydrated as soon as possible in a vacuum dryer or in a current of dry, inert gas, such as nitrogen. The final product is hygroscopic and must be handled, stored and packaged in humidity-controlled rooms. And finally, isopropanol, which is used in large amounts (10 lbs per lb of product) must be separated from water and recovered by fractional distillation. This involved process is further complicated by the fact that aspirin is decomposed by water and by isopropanol, which affects the yield, the purity and the stability of the final product.

Aspirin readily reacts with sodium bicarbonate to form an aqueous solution of the sodium salt. It would therefore appear that the costly and complicated preparation of the sodium salt could be avoided by simply adding aspirin and sodium bicarbonate, in pre-measured amounts corresponding to the desired dose, to a glass of water, stirring the mixture until the aspirin is dissolved and drinking the solution. This would provide aspirin solutions simply and inexpensively, which are free of corrosion-causing insoluble particles to patients on aspirin therapy. And, indeed, such products are commercially available, usually in the form of effervescent tablets containing a mixture of aspirin, sodium bicarbonate and citric acid.

The major drawback of such products is that in order to accomplish dissolution even of the smallest adult dose (325 mg, 5 grains) it was found necessary to use large amount of sodium bicarbonate (1900 mg), which represents a very large excess, since the theroretical amounts needed is only 152 mg. Even allowing for the fact that some of the sodium bicarbonate is neutralized by the citric acid, the amount of the bicarbonate present is equivalent to nearly 40 moles when only one mole is required for the reaction.

Aspirin is usually taken in dosages to two tablets 325 mg each, three times a day. The use of commercial tablets described above would, while giving particle-free solutions of aspirin, involve ingesting 3,000 mg of elemental sodium per day. This amount of sodium is considered medically detrimental to health in general, but particularly to older patients, and patients with hypertension. As a result, such products are used only for the relief of occasional minor pain or an upset stomach. They are never used on a regular basis by patients with arthritic or those on restricted sodium diets.

In the laboratory or during industrial manufacture, the amount of sodium bicarbonate used is 46.7 parts per 100 parts of aspirin, whereas in soluble aspirin tablet described above, the amount is 1250 parts, or about 20 times larger. The reason why it is necessary to use such large amounts of sodium bicarbonate in commercial tablets can be explained by the kinetics of the reaction involved.

In the preparation of sodium aspirin, whether in the laboratory or on an industrial scale, the amount of water used is as small as practically possible. Thus, for 100 parts of aspirin and 46.7 parts of sodium bicarbonate, the amount of water is about 50 parts. Therefore, the amount of aspirin is about 50% of the total, the amount of the bicarbonate is about 25% and the amount of water is 25% also. The purpose of using such high concentrations is to utilize the equipment capacity to its maximum, to produce the maximum yield on crystallization and to use the smallest amount of the solvent. Also, the use of high concentrations causes the reaction to be completed in shorter time, since the rate of a chemical reaction is proportional to the product of the concentrations of the reactants. In the present case, the rate can be expressed by the equation:

$$R = C_1 \times C_2$$

where R is the rate and $C_1$ and $C_2$ are the concentrations of aspirin and sodium bicarbonate, respectively.

The concentration of both reactants varies constantly as the reaction proceeds. The initial concentration of aspirin is low because of its low solubility, whereas that of the more soluble sodium bicarbonate is about 33%.

The situation is quite different when the use of single doses by individual patients is considered. Aspirin tablets are taken with a half-glass of water about 100 to 120 ml; about 3½ to 4 oz). While the concentration of aspirin is the same in any amount of water, its value being determined by its solubility in water (0.33%) and is thus constant, the concentration of sodium bicarbonate ($C_2$ in the above equation) can be varied as desired within relatively wide limits. However, if one wishes to use it in equimolecular proportions, a 325 mg dose of aspirin will require 152 mg of sodium bicarbonate to produce a solution. If this dose is taken in 100 ml of water, the concentration of sodium bicarbonate will be, initially, 0.152% and will decrease as the reaction progresses. Thus, concentration values in the laboratory or the plant, on one hand, and in personal usage on the other, are 33% vs. 0.15%. Referring to the equation above, it is evident that the rate of the reaction in the later case will be very much lower than in the former.

In order to bring the rate of the reaction within practical limits, and since it is not possible to increase the concentration of aspirin, the only alternative is to increase the concentration of sodium well beyond the stoichiometric proportions. As pointed out, the sodium content of such soluble aspirin products is so high as to make them unsuitable for most of the major applications of aspirin in medicine.

The influence of sodium bicarbonate concentrations on its rate of reaction with aspirin was determined by stirring 325 mg of aspirin with variable amounts of sodium bicarbonate in 100 ml of water and recording the time needed for the formation of a solution. Aspirin USP mesh #325 was used. This is the finest particle size available commercially (Monsanto, "micronized"). In order to simulate the conditions of practical use as closely as possible, the mixture gas stirred by hand and with a teaspoon in an 8 oz glass.

TABLE 1

| sodium bicarbonate (mg) | 2,000 | 1,000 | 500 | 250 | 152 |
|---|---|---|---|---|---|
| reaction time (minutes) | 0.5 | 1.0 | 2.2 | 5.5 | 12 |

In order to be of practical use to individual patients, a dose of a soluble aspirin product should dissolve in about half a glass of water (100–120 ml; 3- ½-4 oz), in a reasonably short time (less than 60 seconds), with stirring by hand with a spoon. As mentioned, this is achieved in commercial products by the use of a large excess of sodium bicarbonate. The necessity for such an excess is also seen when Table 1 is examined. However, the price is the introduction of amounts of sodium that are unacceptable, if the product is to be used on a regular basis. As can also be seen from Table 1, if the sodium bicarbonate is reduced to its theoretical amount (the minimum necessary for the reaction is 152 mg) the reaction rate becomes unacceptably low (12 minutes).

SUMMARY OF THE INVENTION

The object of the present invention is to provide a soluble aspirin composition which dissolves in water in less than 60 seconds and which contains the theoretical amount of neutralizing agent.

It was discovered, and is the substance of the present invention, that the reaction between aspirin and alkaline compounds, such as sodium and potassium bicarbonates, sodium and potassium tri-citrates and the like, is catalyzed by surface-active agents. Even in high dilutions, such as about 0.125–0.325% by weight and using only equimolecular amounts of reactants, it was discovered that this catalytic effect can reduce the time of the reaction from about 10 minutes to 30–40 seconds, thus making this reaction suitable for the practical purposes mentioned above.

The mechanism of the catalysis in the present case probably involves as a first stage, the attraction and attachment of the hydrophobic groups of the surfactants to aspirin molecules and similar attraction and attachment of hydrophilic groups to the alkaline reactants. This brings the molecules of aspirin and alkaline compounds into close contact and make possible their rapid interaction even in dilute solutions.

The various features of novelty which characterize the invention are pointed out with particularity in the claims annexed to and forming a part of this disclosure. For a better understanding of the invention, its operating advantages and specific objects attained by its uses, reference is made to the following descriptive matter in which the preferred embodiments of the invention are illustrated.

DESCRIPTION OF THE PREFERRED EMBODIMENTS

In the following, several examples will be given of various compositions and methods covered by the present invention.

Lecithin is an example of a natural product which acts as a surfactant and will illustrate this invention.

EXAMPLE 1

Four grams of aspirin (Monsanto, micronized), 1.87 gm of sodium bicarbonate and 0.7 gm of lecithin ("Alcolec", American Lecithin Co. Inc.) were intimately mixed in a blender. In this composition the amount of sodium bicarbonate is one that is theoretically needed to neutralize the aspirin (molar ratio: 1 to 1).

533 mg of this mixture (containing 325 mg of aspirin and 152 mg of sodium bicarbonate) were stirred with 100 ml of water, using hand-stirring with a teaspoon. The aspirin was dissolved in 30 seconds. The resulting solution was translucent, since lecithin forms colloidal suspensions rather than true solutions. Lecithin is particularly suitable in the present application, since, unlike synthetic surface-active agents, it is an edible, digestible constituent of a number of foods.

Similarly to lecithin, certain organic polymers containing hydrophobic and hydrophilic groups are effective in the practice of this invention. Among the polymers which combine high effectiveness with low toxicity are oxyethylene-oxypropylenes of the following structure:

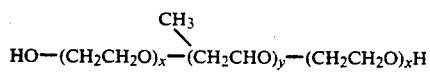

These polymers are commercially available under the tradenames of "PLURONIC" (oxypropylene group in the center, as shown above, "PLURONIC R" (oxypropylene groups at both ends) and "TETRONIC" (containing oxypropylene and amino groups). All are very effective increasing the rate of reaction between aspirin and neutralizing agents. Example 2 illustrates the use of these polymers.

EXAMPLE 2

Four grams of aspirin (Monsanto, micronized), 1.87 gm of sodium bicarbonate and 0.7 gm of PLURONIC F108 (BASF Co.) were intimately mixed in a blander.

533 mg of this mixture (containing 325 mg of aspirin and 152 mg of sodium bicarbonate) were stirred with 100 ml of water as described in Example 1. A clear solution resulted in 30-40 seconds.

The effectiveness of oxyethylene-oxypropylene polymers in increasing the rate of reaction between aspirin and neutralizing agents is about the same, regardless of the length of the chain (x and y in the above formula). However, for practical purposes, the solid polymers are preferred such as PLURONIC F108, F127, F68; PLURONIC 10R8, 25R8; TETRONIC 908, 909, 1107; and TETRONIC 90R8, 110R7, 150R8.

The toxicity of these polymers is very low and, for the types mentioned, ranges from oral $LD_{50}$ 2gm/kg to 15gm/kg.

Other polymers of low toxicity, for example Polysorbate 60 NF, give equally satisfactory results.

Neutralizing agents other than sodium bicarbonate can be used. The following example illustrates the use of potassium bicarbonate.

EXAMPLE 3

Four grams of aspirin (Monsanto, micronized), 2.23 gm of potassium bicarbonate and 0.7 gm of PLURONIC F108 were intimately mixed in a blender.

563 mg of this mixture (containing 325 mg of aspirin and 180 mg of potassium bicarbonate; molar ratio 1 to 1) were stirred with 100 ml of water, as described. A clear solution resulted in 30-40 seconds.

It is not necessary to use micronized aspirin in this invention. Coarser particle size can be used, provided that the blender is efficient enough to reduce the mixture to a fine powder. This is illustrated in further examples.

The usual excipients, dispersants, diluents and bulking agents can be used in formulating compositions of the present invention. For example: sucrose, dextrose, mannitol, sorbitol and the like may be added to the composition.

In order to have aspirin, the alkaline compound and the surfactant in the form of a single mixture, as shown in Examples 1, 2 and 3, it is necessary to have each component in a bone-dry condition, since aspirin is sensitive to moisture. However, commercial surfactants used in the present invention, such as lecithin, PLURONIC, TETRONIC and others, contain small amounts of moisture, usually on the order of about 1%, enough to destabilize aspirin and render the entire composition unstable over a certain period of time. In addition, even if the components are thoroughly dry, it is necessary to prevent intimate contact among the components since they tend to interact in a dry state also. This can be accomplished by means well-known in the art of formulation, such as coating the particles with inert substances (for example, polyvinylpyrrolidone, magnesium stearate, lactose, dextrose and the like). Modern fluid beds are particularly efficient in such coating operations.

However, the extreme drying of ingredients and the coating operations which are necessary to insure the shelf-stability of the compositions of this invention are very costly and substantially increase the cost of the finished product. These operations and attendant expenses can be avoided and the product of this invention manufactured much more economically, by simply keeping the aspirin separated from other ingredients and combining them at the time of use. Example 4 and several others illustrate this case, as well as the use of diluents.

EXAMPLE 4

2.33 gm of sodium bicarbonate, 0.40 gm of PLURONIC F108 and 5.77 gm of sucrose were ground together into a fine powder.

550 mg of this mixture (containing 151 mg of sodium bicarbonate) and 325 mg of aspirin (micronized) were added to 100 ml of water and stirred with a teaspoon. A clear solution resulted in 30-40 seconds. (The quantities used in this example are equimolar).

EXAMPLE 5

5 gm of aspirin (mesh #80) were mixed with 3.5 gm of sucrose and mixed in a blender until a fine powder was obtained (Mixture "A"). 8.5 gm of sodium bicarbonate and 1 gm of PLURONIC F108 were similarly reduced to a fine powder (Mixture "B").

550 mg of "A" (containing 325 mg of aspirin) and 160 mg of "B" (containing 152 mg of sodium bicarbonate, molar ratio 1 to 1) were added to 100 ml of water with stirring. A clear solution resulted in 30 seconds.

EXAMPLE 6

3 gm of TETRONIC 908 and 3 gm of sucrose were blended as described in example 5. 550 mg of this mixture "A" (Example 5, containing 325 mg of aspirin), 152 mg of sodium bicarbonate and 100 mg of the surfactant mixture prepared above, were added to 100 ml of water with stirring. A clear solution resulted in 30-40 seconds.

The use of aspirin mesh #80 is very convenient because, unlike the micronized type, it is free-flowing and is much easier to handle. In commercial products the micronized type is often used, presumably because the fine particles are less damaging to the gastrointestinal mucosa. There is no clinical evidence to support this. On the contrary, the medical reports concerning the damage were all based on the use of commercial aspirin products.

In commonly used dosages, such as 325-500 mg, aspirin is an effective analgesic. However, at these levels it only relieves the symptoms of arthritis (pain) and does little to affect the cause of this disease, which is inflammation. In order to relieve the latter, aspirin must be used in much larger doses. Indeed, at about 6 gm per day, aspirin is considered to be the most effective non-steroidal anti-inflammatory agent known at present (International Journal of Experimental and Clinical Pharmacology, 1982).

However, the side-effects of aspirin, which are quite severe already at low levels, become considerably more serious when the dose is increased from 325-500 mg to 6,000 mg. In particular, the older patients, who are especially in need of large, anti-inflammatory doses, are also the ones who are the most vulnerable to their side effects. Yet, aspirin is the drug of choice in arthritis and about half of all the aspirin used, is used by older patients. Obviously, to have such large doses available in the much safer solution form would be very desirable. The present invention is applicable to the preparation of such concentrated solutions of aspirin.

EXAMPLE 7

Two grams of aspirin (Monsanto, micronized), 0.93 gm of sodium bicarbonate and 0.35 gm of PLURONIC F108 were reduced in a blender into a fine powder. This composition was stirred with 100 ml of water and gave a clear solution in 30-40 seconds.

The formation of a solution is accompanied by considerable foaming due to the evolution of carbon dioxide and, therefore, it is preferable to use a larger amount of water, for example 150 ml.

If, in this example, the surfactant is omitted, the dissolution takes about 10 minutes, showing the effect of the surfactant on the rate of the reaction.

EXAMPLE 8

Five grams of aspirin (mesh #80), 2.8 gm of sodium bicarbonate 0.4 gm of PLURONIC F108 and 10.3 gm of sucrose were blended into a fine powder. 7.4 gm of this mixture (containing 2 gm of aspirin) were mixed with 150 ml of water. After about 30 seconds of stirring there resulted a clear solution.

As mentioned earlier, if the material used are not completely dry it is preferable to keep the composition containing aspirin separated from other ingredients, as illustrated in the following example.

EXAMPLE 9

Five grams of aspirin (mesh #80) and 3.5 gm of sucrose were reduced to a fine powder in a blender, (Mixture "A"). A second mixture was prepared separately by similarly blending 2.8 gm of sodium bicarbonate, 0.4 gm of PLURONIC F108 and 6.8 gm of sucrose (Mixture "B"). 3.4 gm of mixture "A", containing 2 gm of aspirin, and 3.4 gms of mixture "B" containing 0.95 gm of sodium bicarbonate, were stirred with 100 ml of water. A clear solution resulted in about 30 seconds.

Although only a theoretical amount of sodium bicarbonate is used in Examples 7, 8, and 9, the amount of sodium it represents is 252 mg, which may be too high for patients on a restricted sodium regimen. In this case, it is preferable to use a sodium-free neutralizing agent, such as potassium bicarbonate.

EXAMPLE 10

The mixture of aspirin with sucrose was prepared as described in Example 9 (Mixture "A"). A second mixture was prepared separately by intimately mixing 3.3 gm of potassium bicarbonate, 0.4 gm of PLURONIC F108 and 6.3 gm of sucrose in a blender. (Mixture "B").

550 mg of mixture "A" (containing 325 mg of aspirin) and 550 mg of mixture "B" (containing 181 mg of potassium bicarbonate) were stirred with 100 ml of water. A clear solution resulted in 30 seconds.

By using 3.3 gm of each mixture, as described in Example 9, a solution containing 2 gm of aspirin is similarly obtaining in 30-40 seconds. This concentrated solution of potassium acetylsalicylate has a very slight bitter taste, but is palatable.

As was mentioned earlier, surface-active agents, such as lecithin and oxyethylene-oxypropylene polymers, are very effective in increasing the rate of the reaction between aspirin and sodium bicarbonate as shown in the preceding examples. They were equally effective in the reaction between aspirin and potassium bicarbonate. The agent used in most of the experiments was PLURONIC F108. It was selected at random because there was little difference in the activity of these surface-active agents and not because it offered any special advantages.

Although the use of solid surface-active agents is preferred in the present invention, they are used in such minor amounts that the use of liquids or pastes is not excluded. The following example illustrates the use of a liquid surfactant.

EXAMPLE 11

Five grams of aspirin mesh #80 and 3.5 gm of sucrose were mixed in a blender, as described (Mixture "A"). 2.8 gm of sodium bicarbonate, 6.8 gm of sucrose and 0.4 gm of polysorbate (60 NF) were similarly blended. The resulting mixture (Mixture "B") was slightly sticky, but free-flowing and easy to handle.

3.4 gm of mixture "A" (containing 2 gm of aspirin) and 3.4 gm of mixture "B" (containing 0.95 gm of sodium bicarbonate) were stirred with 150 ml of water. A clear solution resulted in 30-40 seconds.

If the polysorbate is omitted in the mixture "B", the formation of solution required about 10 minutes.

The use of water-soluble surface-active agents is, for evident reasons, much preferred. But surprisingly water-insoluble agents are about equally effective. Example 1 showed the use of lecithin, which is insoluble in water, but forms a translucent colloidal solution or suspension. The following example illustrates the use of another water-insoluble surfactant, glycerol monostearate. The product used is commercially available under the tradename GMS-FG from Mazer Chemicals, Division of PPG Industries, Inc.

EXAMPLE 12

5 gm of aspirin mesh #80 were blended with 0.25 gm of GMS-FG as described in previous examples (Mixture "A").

525 mg of mixture "A" (containing 500 mg of aspirin) and 233 mg of sodium bicarbonate (theory: 233 mg) were stirred with 100 ml of water. The aspirin went into solution within about 30 seconds. The solution was not clear and had a slight amount of glycerol monostearate suspended in it.

Weakly alkaline compounds, other than the bicarbonates of alkaline metals, can be used to react with aspirin in the present invention, for example: sodium and potassium tri-citrates, basic amino acids (lysine, ornithine, arginine) and their carbonates, bicarbonates and carbamates. The following example illustrates the use of potassium citrate.

EXAMPLE 13

550 mg of mixture "A" (Example 9) containing 325 mg of aspirin, were blended with 585 mg of potassium tri-citrate mono-hydrate (molar ratio: 1 to 1). This mixture was added to 100 ml of water containing 0.3 gm of Polysorbate 60 NF. A clear solution resulted in 30-35 seconds.

Human stomach fluids contain a strong acid (hydrochloric acid) and it is known that salts of aspirin are converted by strong acids to acetylsalicylic acid (aspirin). It was thus important to ascertain whether or not solutions prepared by the present invention, and which contain such salts, would form insoluble particles of aspirin on contact with hydrochloric acid, thus nullifying the major purpose the this invention. It was equally important, for comparison to study the behavior of regular aspirin in the presence of this acid.

The concentration of gastric hydrochloric acid is about 0.1N and the average volume of gastric fluids is about 20 ml. Each solution prepared in the above examples, except Examples 1 and 12, was added to 20 ml of hydrochloric acid 0.1N. (Example 1 and 12 were exclude because neither was a clear solution, due to the presence of an insoluble surfactant). In every case, on mixing with hydrochloric acid, there resulted a clear solution free of any insoluble particles. In each case the solution was under observation for 3 to 4 hours and in each case the solution remained clear.

Solid dosage forms of aspirin (tablets and capsules) are usually taken with water and, consequently, the experiments which are describe here were performed to reflect and simulate this as closely as possible. Aspirin (micronized or mesh #80), in amounts ranging from 325 mg to 2,000 mg, was stirred with 100-120 ml of water (about half a glass, about 4 oz), the suspension was added to 20 ml of hydrochloric acid (0.1N) and the mixture was stirred continuously by hand or, with longer time periods, with a magnetic stirrer.

With amounts of 325 mg. of aspirin, about 10 minutes was required to reduce the insoluble solid to a relatively small quantity (about 50 mg). The amount of time needed to obtain a clear solution was about 20 minutes. With amounts of 500 mg and over, it was not possible to obtain a solution after 3 hours of stirring, as the solubility limit was reached at about 330 mg.

It must be pointed out that, in the stomach, aspirin in not under conditions of constant stirring in suspended, dispersed state as described in the above experiments. Gastroscopic studies show that most of the drug, especially when taken in tablet form, adheres to the stomach mucosa and also settles in stomach crevices (rugae) and thus largely escapes suspension and agitation. If, in experiments described above using aspirin alone, the stirring is omitted, the particles of aspirin remain undissolved for over 24 hours of observation.

The foregoing experiments illustrate the profound and pharmacologically vital difference between the commercial form of aspirin and aspirin solutions of the present invention. In the presence of hydrochloric acid in concentrations and amounts present in the stomach, commercial aspirin remains undissolved for long periods of time and thus, in a condition to cause damage to the gastrointestinal tract. In contrast, under the same conditions aspirin solutions of the present invention remain clear and free of the damage-causing insoluble particles for long periods of time, during which absorption from the gastrointestinal tract takes place.

This safer form of aspirin permits the utilization of the full range of aspirin's therapeutic activities, i.e. analgesic, anti-inflammatory and heart attack preventive, particularly for patients who are vulnerable to its side effect. Solutions of aspirin salts of the present invention have other advantages. For example, they can be taken by patients who have difficulties with swallowing tablets, which is a common condition with the elderly because of weakening of the muscles of the esophagus. Further, clinical tests show that aspirin solutions are absorbed much faster than aspirin in solid form, thus affording a faster relief from the pain and inflammation ("The Salicylates", by Smith & Smith; John Wiley & Sons Publishers). Also, because of the faster absorption, any possible damage to the gastrointestinal mucosa is also minimized due to a shorter residence time in the gastrointestinal tract.

It should be mentioned that surface-active agents, specifically wetting agents, are often used in the formulation of pharmaceutical tablets. Their presence is needed to counteract certain properties imparted to the tablet by the lubricants which are used to prevent the jamming of the punch by the particles of the formulation adhering to the die. The lubricants used most often are magnesium stearate and hydrogenated vegetable oils. Since these substances are insoluble in water and, in addition, are highly hydrophobic, they cause the tablet to repel water and as a result the tablet disintegrates very slowly and its therapeutic action is much delayed. It is in order to reduce as much as possible this hydrophobic effect of lubricants that small amounts of wetting agents, such as polysorbate 20 or sodium alkyl sulfates, are incorporated into the tabletting formulation. In no case have wetting agents been used in combination with soluble alkalizing substances to rapidly solubilize equimolar amounts of aspirin, as disclosed in the present invention.

While the specific embodiments of the invention have been shown and described in detail to illustrate the application of the principles of the invention, it will be understood that the invention may be embodied otherwise without departing from such principles.

What is claimed is:

1. An aspirin containing composition which is readily dissolvable in water in less than 60 seconds, comprising: aspirin;
   a surfactant having low toxicity, the surfactant being selected from the group consisting of lecithin polysorbate, glycerol monosterate, and oxyethyleneoxypropylene polymers, there being at least 0.125% by weight surfactant; and
   and alkaline compound for reacting with and neutralizing the aspirin in water, the relative amount of aspirin and alkaline compound being equimolar and being selected to substantially correspond to the theoretical neutralizing amounts thereof.

2. A method of increasing the rate of reaction between aspirin and an alkaline compound in aqueous medium comprising adding at least 0.125% by weight of a surfactant to the aspirin and alkaline compound in the aqueous medium, providing the aspirin and alkaline compound in equimolar amounts which substantially correspond to theoretical neutralizing amounts thereof, the aspirin dissolving in the aqueous medium in less than 60 seconds, the surfactant being selected from the group consisting of lecithin, polysorbate, glycerol monostearate, and oxyethylene-oxypropylene polymers 3. A composition according to claim 2 wherein the alkaline compound comprises the bicarbonate or tricitrate of an alkaline metal.

4. A composition according to claim 2 wherein the alkaline compound is selected from the group consisting of sodium bicarbonate, potassium bicarbonate, sodium tricitrate and potassium tricitrate.

5. A composition according to claim 2 wherein the alkaline compound is selected from group consisting of basic amino acids, and carbonates, bicarbonates and carbamates thereof.

6. A composition according to claim 2 wherein the alkaline compound is selected from the group consisting of lysine, ornithine and arginine.

7. A composition according to claim 2 including at least one of an excipient, a dispersant, a diluent and a bulking agent.

8. A composition according to claim 7 including at least one of an excipient, a dispersant, a diluent and a bulking agent selected from the group consisting of sucrose, dextrose, mannitol and sorbitol.

9. A composition according to claim 2 wherein the aspirin is in particle form and is coating with inert substance.

10. A composition according to claim 16 wherein the inert substance is selected from the group consisting of polyvinylpyrrolidone, magnesium stearate, lactose and dextrose.

11. A composition according to claim 2 including a mixture of the alkaline compound and the surfactant and a separate component including the aspirin which is held separate from the mixture before use with water.

12. A composition according to claim 11 wherein at least one of the mixture and the component included sucrose.

13. A method according to claim 2 including mixing the alkaline compound and the surfactant in a dry mixture and thereafter mixing the dry mixture with aspirin in particle form with the aqueous medium.

* * * * *